United States Patent [19]

Cade et al.

[11] Patent Number: 5,620,704
[45] Date of Patent: Apr. 15, 1997

[54] PROCESS FOR STABILIZING GELATIN PRODUCTS

[75] Inventors: Dominique Cade, Colmar; Nicolas Madit, Mulhouse, both of France

[73] Assignee: Warner-Lambert Company, Morris Plains, N.J.

[21] Appl. No.: 334,974

[22] Filed: Nov. 7, 1994

[51] Int. Cl.$^6$ ............................................. A61K 9/64
[52] U.S. Cl. ..................... 424/456; 424/451; 424/460; 424/463; 424/492
[58] Field of Search ......................... 424/456, 451, 424/460; 252/316

[56] References Cited

U.S. PATENT DOCUMENTS

| | | | |
|---|---|---|---|
| 2,467,715 | 4/1949 | White | 106/126 |
| 4,328,119 | 5/1982 | Iwasaki et al. | 252/316 |
| 4,333,849 | 6/1982 | Pack et al. | 252/316 |
| 4,353,809 | 10/1982 | Hoshi et al. | 252/316 |
| 5,376,381 | 12/1994 | Weiner et al. | 424/456 |

FOREIGN PATENT DOCUMENTS

| | | |
|---|---|---|
| 2617047 | 12/1988 | France. |
| 225426 | 6/1984 | Germany. |

OTHER PUBLICATIONS

'Film Compositions for Preparation of Soft Capsules,' *Chemical Abstracts*, vol. 100, No. 26, Jun. 25, 1984, p. 346.

*Primary Examiner*—Thurman K. Page
*Assistant Examiner*—William E. Benston, Jr.
*Attorney, Agent, or Firm*—Charles W. Almer

[57] ABSTRACT

Process for the manufacturing of gelatin products with improved stability against storage under hot and humid conditions and/or aldehydes characterized in that at least one additive, preferred glutamic acid, tryptophan, or nitrilotrismethylene phosphonic acid or a mixture thereof is incorporated into the gelatin before forming the final product as usual as well as the gelatin compositions used and the products obtained by the process.

11 Claims, No Drawings

PROCESS FOR STABILIZING GELATIN PRODUCTS

FIELD OF THE INVENTION

This invention relates to a process for the enhancement of the stability of gelatin products against higher storage temperatures, humidity and/or chemically influenced crosslinking, as well as suitable gelatin compositions and their use in capsule manufacturing or as coating or binding agents of tablets, casing materials and so on.

DESCRIPTION OF THE PRIOR ART

Gelatin is widely used in the pharmaceutical industry as well as in the health food supplement market to manufacture capsules as containers or as coating agents for the capsules or other dosage forms, or as adjuvants or excipients in pharmaceutical preparations like tablets. A primary objective of these dosage forms is to have a good disintegration after being administrated in order to enable a fast dissolution of the active substances in the appropriate digestive organ. Any delay of the disintegration would consequently retard or even reduce the effect of the drug. Consequently, this disintegration characteristic has to remain unchanged over time when finished products are stored prior to use. Extensive dissolution stability testing has been conducted to assess this stability.

Unfortunately, as has been widely described in the literature, the risk for the gelatin product to exhibit a delay in disintegration over time is high. A primary cause of the problem, exposure to certain aldehydes contained in the capsules content at the initial stage or originating from the decomposition of the drug or one of the excipients over time, has been reported in many references as a cause. The mechanism of this chemical interaction named "crosslinking" has been well understood as action of the aldehyde on the free amino groups of the amino acids and especially the lysine and arginine (G. Digenis & al, to be published in J. of Pharm. Sci.). It has also been used further in the sense that overcrosslinking of the gelatin would make it totally insoluble and inappropriate for an enteric dosage form (G. Gutierrez, FR-8201127).

Various patents have been published which deal with this issue. The resistance to crosslinking by formaldehyde can be obtained by chemically modifying the gelatin (succinylated gelatin: Toyo Jozo Co, JP 61/186315 Nippon Elanco Co, JP-61/186314), by adding ions in it (Sanofi, FR-8708828) or silicones (R. P. Scherer, FR-2346/69) or peptides (NITTA, EP-0 335 982).

Another procedure to protect gelatin from crosslinking is to include in the formulation of the drug a formaldehyde scavenger (Teikoku Hormone Mfg Co, JP-168874/1989 and Lion Corporation EP-0 242 855).

Some literature references have also reported that exposure or storage to/under hot and humid conditions is another reason for the delay in the disintegration of gelatin products. These conditions were reported in a temperature range of 25° to 55° C. and a humidity range of 40% to 90% relative humidity. This appears to be very important for most of the pharmaceutical applications of the gelatin where a stability is requested for storage at 40° C. with 75% RH over 3 to 6 months without significant delay in drug dissolution.

This phenomenon was described extensively in the literature, but no proposal has been made to explain the mechanism of the chemical reactions involved in responsible for the poorer dissolution performance of the gelatin: H. W. GOUDA & al., Intl. Jour. Pharmaceutics, 18, 1984, 213–215; S. A. KHALIL & al., Pharmazie, 29 H1, 1974, 36–37; T. C. HAHL & al., Drug Dvpt Industr. Pharmacy, 17 (7), 1991, 1001–1016; M. DEY & al., Pharmaceutical Res., 10 (9), 1993, 1295–1300; K. S. MURPHY & al., Pharm. Techno., March, 1989, 74–82. In the state of the art, no method is known for increasing the resistance of the gelatin to storage at hot and humid conditions as described before.

SUMMARY OF THE INVENTION

The present invention relates to a process for the manufacturing of gelatin products which have improved stability against storage under hot and humid conditions and/or aldehydes in order to improve the dissolution of the gelatin products comprising incorporating additives into the gelatin solution and forming the final product as usual. A further aspect of the invention is the gelatin compositions used for the gelatin products prepared by the process.

DETAILED DESCRIPTION OF PREFERRED EMBODIMENTS

The gelatin to be used with the present invention may be from acid processed pork skin known as A gelatins, from lime processed bones known as B gelatins, from calf skin known as C gelatins, acid processed bones known as AB gelatins or from a combination of two or more of these gelatins.

The additives are selected from the group consisting of ammonium sulfate, ammonium hydrogen sulfate, ammonium hydrogencarbonate, ammonium phosphate, ammonium hydrogenphosphate, ammonium dihydrogenphosphate, ammonium thiocyanate, sodium sulfate, sodium chloride, potassium sulfate, potassium chloride, lithium sulfate, lithium chloride, calcium sulfate, calcium chloride, magnesium sulfate, magnesium chloride, iron (II) sulfate, iron (II) chloride, iron (III) sulfate, iron (III) chloride, manganese (II) sulfate, manganese (II) chloride, glutamic acid, aspartic acid, asparagine, lysine, tryptophane, arginine, guanidine, urea, citric acid, ascorbic acid, ethylenediamine tetraacetate, nitrilotrismethylene phosphonic acid.

The amount of additives is up to 25%, preferably 0.1 to 10% by weight of the dry gelatin. Each additive can be added alone or in combination with one or more additive.

Two types of storage conditions were studied:

1) Hot and humid conditions: temperature varied between 20° and 55° C. and humidity between 40% and 95% RH.

2) Formaldehyde:
   a. Capsules were filled with lactose contaminated by formaldehyde with levels varying between 0–200 ppm, preferably between 1 and 60 ppm. These capsules were either stored in closed bottles at 50° C. up to 2 months or in the open at hot and humid conditions up to 6 months.
   b. Gelatin films were stored in lactose powder contaminated by formaldehyde with level between 0 and 200 ppm, preferably between 1 and 50 ppm. Films are dipped in the contaminated lactose powder in a closed plastic box and kept at 50° C. up to 1 month.

Dissolution measurements:

The dissolution measurements were made with the apparatus described in USP XXII, method II (paddle 50 rpm). The medium was demineralized water at 37° C.±0.5° C. and two procedures were used one for the capsules and one for the gelatin films. The samples are added in the media in a special sinker which prevents them from floating.

1. Capsule dissolution

The capsules are previously stored under one or both of the storage conditions described before. The capsules were filled with Acetaminophen and dissolved in water at 37° C. under agitation (paddle 50 rpm). The percentage of dissolved Acetaminophen is determined by UV spectrophotometry at 300 nm. The required level of dissolved Acetaminophen is higher than 80% at 45 min.

2. Gelatin film dissolution

Films of gelatin are casted on glass plates. These films are stored at one or both of the conditions described before. The films are then added in demineralized water at 37° C. under agitation (paddle 50 rpm) and the percentage of dissolution is determined by UV spectrophotometry at 217 nm. Uncrosslinked films have a dissolution of more than 90% at 6 min.

The following examples will demonstrate how the addition of inventive compounds increases the resistance of gelatins to crosslinking by hot and humid storage and/or formaldehyde.

EXAMPLE 1

We studied the effect of addition of ammonium sulfate (2% w/w of gelatin) on the resistance of gelatin to formaldehyde crosslinking. Gelatins type a 240 and type B 200 or two different suppliers with two batches each were studies. The gelatin films were casted from a 30% gelatin solution containing 2% w/w of ammonium sulfate ($(NH_4)_2SO_4$) and without additives (Reference). Films were dried at room conditions for 24 hours and dissolution samples were prepared and stored in formaldehyde contaminated lactose powder (at 5 ppm formaldehyde at 50° C. for 1 week).

The dissolution results (%) are summarized in table 1 in comparison to mean values of 4 batches stored for 1 week at room conditions.

TABLE 1

| Gelatin | Supplier | Batch | Reference 3 min | Reference 6 min | $(NH_4)_2SO_4$ 3 min | $(NH_4)_2SO_4$ 6 min |
|---|---|---|---|---|---|---|
| A 240 | A | 1 | 10% | 35% | 80% | 96% |
|  |  | 2 | 7% | 46% | 86% | 98% |
|  | B | 1 | 11% | 60% | 76% | 98% |
|  |  | 2 | 20% | 70% | 60% | 96% |
|  | Mean value for 4 batches |  | 81% | 97% | 74% | 93% |

Table 1 demonstrates a very impressive resistance to formaldehyde crosslinking. Gelatin films with ammonium sulfate have practically the same dissolution results at 3 and 6 min as gelatin films stored at room conditions (mean values for 4 batches). A dramatic decrease in dissolution is noted for films without additives (Reference), especially for dissolution measures at 3 min.

EXAMPLE 2

The effect of addition of nitrilotrismethylene phosphonic acid (AMP, Masquol P320) on the dissolution of gelatin films stored in presence of formaldehyde is studied. The films were prepared by casting a gelatin solution (30% w/w water) containing Masquol P320 (1% w/w gelatin on glass plate and drying at room conditions for 24 hours.

The dissolution samples were then prepared and stored dipped in formaldehyde contaminated lactose in a closed plastic box for 1 week at 50° C. prior to dissolution measurements.

The dissolution results are shown in the following table 2.

TABLE 2

| Gelatin | AMP | Dissolution 3 min | 6 min | 9 min | 12 min | 15 min |
|---|---|---|---|---|---|---|
| A 240 | 0% | 0% | 3% | 10% | 16% | 21% |
|  | 1% | 3% | 15% | 26% | 41% | 52% |
| B 200 | 0% | 8% | 42% | 70% | 84% | 87% |
|  | 1% | 8% | 77% | 89% | 93% | 94% |

Here the beneficial effect of the addition of an additive, Masquol P320, on the resistance of gelatin films to formaldehyde crosslinking is clearly demonstrated.

Effectively, a significant increase in the dissolution of gelatin films was observed for both A 240 films (+150% at 15 min) and B 200 films (+85% at 6 min).

EXAMPLE 3

Gelatin films with amino acids as additives were prepared and stored at hot and humid conditions prior to dissolution measurements. Gelatin films were casted from 30% w/w solution containing either 1% Tryptophan or 1% Glutamic acid. Gelatin films of A 240 and of B 200 were prepared. Films were dried at room conditions for 24 hours prior to sample preparation. The samples were stored at 50° C. and 80% RH for 3 (A240) or 4 months (B 200) prior to dissolution measurements. The results are shown in table 3 in comparison with gelatin without additives stored at room temperature (Ref.).

TABLE 3

(Storage 50° C./80% RH for 3 (A 240) and 4 months (B 200)

| Gelatine | Additive | Dissolution (%) after minutes 3 | 6 | 9 | 12 | 15 |
|---|---|---|---|---|---|---|
| A 240 | 0% | 6% | 8% | 14% | 36% | 67% |
|  | 1% Glu | 6% | 50% | 92% | 99% | 100% |
|  | 1% Trp | 10% | 87% | 97% | 99% | 100% |
| B 200 | 0% | 3% | 76% | 92% | 98% | 98% |
|  | 1% Glu | 54% | 92% | 97% | 99% | 100% |
|  | 1% Trp | 59% | 97% | 100% | 100% | 100% |
| A 240 | 0% Ref. | 72% | 96% | 99% | 100% | 100% |
| B 200 | 0% Ref. | 96% | 100% | 100% | 100% | 100% |

The dissolution results, compared with reference tests, demonstrate that the addition of amino acids, specifically Glutamic acid and Tryptophan at 1% level (in respect of dry gelatin) increases the dissolution of gelatin films especially at 3 min for B 200 and 9 min for A 240 gelatins.

In both cases, we reached the total dissolution of gelatin films (100% dissolution) more rapidly with additives than with reference films stored at the same conditions.

EXAMPLE 4

Gelatin films with salts or organic compounds were prepared as in example 3. The following products were added at 1% level compared to dry gelatin weight: urea and Masquol P320 (AMP).

The dissolution measurements were performed as for example 3 and results are summarized in following table 4:

TABLE 4

| Gelatine | Additive | Dissolution (%) after minutes | | | | |
|---|---|---|---|---|---|---|
| | | 3 | 6 | 9 | 12 | 15 |
| A 240 | 0% | 6% | 8% | 14% | 36% | 67% |
| | 1% Glu | 10% | 92% | 99% | 100% | 100% |
| | 1% AMP | 94% | 97% | 100% | 100% | 100% |
| B 200 | 0% | 3% | 76% | 92% | 98% | 98% |
| | 1% Urea | 79% | 97% | 99% | 100% | 100% |
| | 1% AMP | 77% | 94% | 99% | 100% | 100% |
| A 240 | 0% Ref. | 72% | 96% | 99% | 100% | 100% |
| B 200 | 0% Ref. | 96% | 100% | 100% | 100% | 100% |

The addition organic compounds (Urea, Masquol P320) increased significantly the dissolution of gelatin films of both type A 240 and B 200.

For A 240 the 100% dissolution is obtained at about 6 min compared to only 8% dissolution for gelatin films without additives. This result is comparable to reference films (Ref.) stored at normal conditions. The dissolution is higher than 75% for B 200 gelatin after only 3 min (3% for B 200 films without additives). These results are comparable to reference B 200 films (Ref.) stored at normal conditions.

As demonstrated from these examples, the incorporation of selected additives into the gelatin films increases the resistance of gelatin films and capsules to crosslinking in presence of aldehydes or when stored in hot and humid conditions.

EXAMPLE 5

The dissolution of capsules containing additives and filled with lactose contaminated by formaldehyde (5 ppm or 20 ppm) and stored at 50° C. in closed bottles for 1 or 2 months was studied. The results are expressed as the level of dissolution of acetaminophen filled in the capsules and measured according to the USP XXII Method 2.

TABLE 5

| Test | Additive | Dissolution (%) after minutes | | | | |
|---|---|---|---|---|---|---|
| | | 15 | 30 | 45 | 60 | 75 |
| A | 0% | 12% | 40 | 57% | 71% | 79% |
| | 2% (I) | 39% | 68% | 87% | 95% | 97% |
| B | 0% | 24% | 50% | 66% | 78% | 88% |
| | 2% (I) | 40% | 72% | 90% | 98% | 100% |
| | 1% (II) | 39% | 79% | 95% | 100% | 100% |
| C | 0% | 43% | 79% | 94% | 98% | 99% |

Test A: Storage 4 weeks at 50° C., 20 ppm formaldehyde
Test B: Storage 2 months at 50° C., 5 ppm formaldehyde
Test C: Reference storage at room conditions
Additive (I): Ammoniumsulfate
Additive (II): Aspartic acid The dissolution of capsules containing additives is better than the reference one. This dissolution is equal to the dissolution of a standard capsules stored at room conditions.

While there have been described what are presently believed to be the preferred embodiments of the invention, those skilled in the art will realize that various changes and modifications may be made to the invention without departing from the spirit of the invention, and it is intended to claim all such changes and modifications as fall within the scope of the invention.

We claim:

1. A process for the manufacturing of gelatin products with improved stability for storage under hot and humid conditions and/or aldehydes comprising the steps of:

incorporating at least one additive selected from the group consisting essentially of ammonium sulfate, ammonium hydrogen sulfate, ammonium hydrogencarbonate, ammonium phosphate, ammonium hydrogenphosphate, ammonium dihydrogenphosphate, ammonium thiocyanate, sodium sulfate, sodium chloride, potassium sulfate, potassium chloride, lithium sulfate, lithium chloride, calcium sulfate, calcium chloride, magnesium sulfate, magnesium chloride, iron (II) sulfate, iron (II) chloride, iron (III) sulfate, iron (III) chloride, manganese (II) sulfate, magnanese (II) chloride, glutamic acid, aspartic acid, asparagine, lysine, tryptophane, arginine, guanidine, urea, citric acid, ascorbic acid, ethylenediamine tetraacetate, nitrilotrismethylene phosphonic acid or mixtures thereof into gelatin before forming a final gelatin product; and forming a final gelatin product.

2. A process according to claim 1 wherein the additive or the mixture of additives is incorporated in the gelatin in an amount of up to 25%.

3. A process according to claim 2, wherein the additive or the mixture of additives is incorporated in the gelatin in an amount of from about 0.1 to about 10% by weight of the dry gelatin.

4. A process according to claim 3 for the manufacture of gelatin films, capsules, casings or coatings.

5. A gelatin composition containing additives with improved stability for storage under hot and humid conditions and/or aldehydes, comprising at least one additive selected from the group consisting essentially of ammonium sulfate, ammonium hydrogen sulfate, ammonium hydrogencarbonate, ammonium phosphate, ammonium hydrogenphosphate, ammonium dihydrogenphosphate, ammonium thiocyanate, sodium sulfate, sodium chloride, potassium sulfate, potassium chloride, lithium sulfate, lithium chloride, calcium sulfate, calcium chloride, magnesium sulfate, magnesium chloride, iron (II) sulfate, iron (II) chloride, iron (III) sulfate, iron (III) chloride, manganese (II) sulfate, manganese (II) chloride, glutamic acid, aspartic acid, asparagine, lysine, tryptophane, arginine, guanidine, urea, citric acid, ascorbic acid, ethylenediamine tetraacetate, nitrilotrismethylene phosphonic acid or a mixture thereof.

6. A gelatin product prepared from compositions with improved stability for storage under hot and humid conditions and/or aldehydes comprising at least one additive selected from the group consisting essentially of ammonium sulfate, ammonium hydrogen sulfate, ammonium hydrogencarbonate, ammonium phosphate, ammonium hydrogenphosphate, ammonium dihydrogenphosphate, ammonium thiocyanate, sodium sulfate, sodium chloride, potassium sulfate, potassium chloride, lithium sulfate, lithium chloride, calcium sulfate, calcium chloride, magnesium sulfate, magnesium chloride, iron (II) sulfate, iron (II) chloride, iron (III) sulfate, iron (III) chloride, manganese (II) sulfate, manganese (II) chloride, glutamic acid, aspartic acid, asparagine, lysine, tryptophane, arginine, guanidine, urea, citric acid, ascorbic acid, ethylenediamine tetraacetate, nitrilotrismethylene phosphonic acid or a mixture thereof.

7. A gelatin product according to claim 6, wherein said gelatin product comprises a gelatin film, capsule, casing or coating.

8. A gelatin product according to claim 6, wherein said gelatin film, capsule, casing or coating comprises 0.1 to 10% by weight of at least one additive of the group consisting of urea, tryptophan, glutamic acid or nitrilotrismethylene phosphonic acid or mixtures thereof.

9. A pharmaceutical gelatin capsule shell prepared from compositions with improved stability for storage under hot and humid conditions and/or aldehydes comprising at least one additive selected from the group consisting essentially of ammonium sulfate, ammonium hydrogen sulfate, ammonium hydrogencarbonate, ammonium phosphate, ammonium hydrogenphosphate, ammonium dihydrogenphosphate, ammonium thiocyanate, sodium sulfate, sodium chloride, potassium sulfate, potassium chloride, lithium sulfate, lithium chloride, calcium sulfate, calcium chloride, magnesium sulfate, magnesium chloride, iron (II) sulfate, iron (II) chloride, iron (III) sulfate, iron (III) chloride, manganese (II) sulfate, manganese (II) chloride, glutamic acid, aspartic acid, asparagine, lysine, tryptophane, arginine, guanidine, urea, citric acid, ascorbic acid, ethylenediamine tetraacetate, nitrilotrismethylene phosphonic acid or a mixture thereof.

10. A pharmaceutical gelatin capsule shell containing 0.1 to 10% by weight of at least one additive of the group consisting essentially of ammonium sulfate, ammonium hydrogen sulfate, ammonium hydrogencarbonate, ammonium phosphate, ammonium hydrogenphosphate, ammonium dihydrogenphosphate, ammonium thiocyanate, sodium sulfate, sodium chloride, potassium sulfate, potassium chloride, lithium sulfate, lithium chloride, calcium sulfate, calcium chloride, magnesium sulfate, magnesium chloride, iron (II) sulfate, iron (II) chloride, iron (III) sulfate, iron (III) chloride, manganese (II) sulfate, manganese (II) chloride, glutamic acid, aspartic acid, asparagine, lysine, tryptophane, arginine, guanidine, urea, citric acid, ascorbic acid, ethylenediamine tetraacetate, nitrilotrismethylene phosphonic acid or a mixture thereof urea, tryptophan, glutamic acid or nitrilotrismethylene phosphonic acid or mixtures thereof.

11. A pharmaceutical gelatin capsule shell according to claim 10 containing 0.1 to 10% by weight of at least one additive of the group consisting essentially of urea, tryptophan, glutamic acid of nitrilotrismethylene phosphonic acid or mixtures thereof.

* * * * *